(12) United States Patent
Bodner

(10) Patent No.: US 11,931,545 B2
(45) Date of Patent: Mar. 19, 2024

(54) DRUG INFUSION PORT

(71) Applicant: Medtronic, Inc., Minneapolis, MN (US)

(72) Inventor: Jeffrey Bodner, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 367 days.

(21) Appl. No.: 17/085,562

(22) Filed: Oct. 30, 2020

(65) Prior Publication Data
US 2022/0133991 A1 May 5, 2022

(51) Int. Cl.
*A61M 5/142* (2006.01)
*A61M 5/178* (2006.01)
*A61M 39/02* (2006.01)

(52) U.S. Cl.
CPC ........ *A61M 5/14276* (2013.01); *A61M 5/178* (2013.01); *A61M 39/0208* (2013.01); *A61M 2005/14284* (2013.01); *A61M 2039/0238* (2013.01); *A61M 2205/3317* (2013.01);
(Continued)

(58) Field of Classification Search
CPC ...... A61M 5/14276; A61M 2205/3317; A61M 2005/14284; A61M 2205/3553; A61M 2205/502; A61M 39/0208; A61M 2039/0238; A61M 2205/8243; A61M 2039/0244; A61M 2205/35; A61M 2205/3523; A61M 39/0247; A61M 39/02; A61M 2205/04; A61M 2039/0267; A61M 2039/0282; A61M 2039/0291; A61B 34/20; A61B 2034/2051; A61B 2034/731; A61B 5/062; A61B 5/065; A61N 1/37229
See application file for complete search history.

(56) References Cited

U.S. PATENT DOCUMENTS

| | | |
|---|---|---|
| 5,045,064 A | 9/1991 | Idriss |
| 5,085,644 A | 2/1992 | Watson et al. |
| 5,281,210 A | 1/1994 | Burke et al. |

(Continued)

FOREIGN PATENT DOCUMENTS

| | | |
|---|---|---|
| WO | WO0066204 A1 | 11/2000 |
| WO | WO2009129474 A1 | 10/2009 |

(Continued)

OTHER PUBLICATIONS

Alcyone Lifesciences, Inc., Bringing Hope to Spinal Muscular Atrophy (SMA) Patients with the Alcyone Lifesciences ThecaFlex DRxTM System Breakthrough Device, Dec. 2, 2019, 3 pages, available at: https://www.prnewswire.com/news-releases/bringing-hope-to-spinal-muscular-atrophy-sma-patients-with-the-alcyone-lifesciences-thecaflex-drx-system-breakthrough-device-300967222.html.

*Primary Examiner* — Lauren P Farrar
*Assistant Examiner* — Kathleen Paige Farrell
(74) *Attorney, Agent, or Firm* — Husch Blackwell LLP

(57) ABSTRACT

A medical system configured to aid a user in locating an access port of an implantable medical device, the medical system including an implantable port comprising a medicament chamber accessible through a septum, a localizer base operably coupled to the implantable port comprising an array of electromagnetic field emitting coils, an antenna array comprising a plurality of electromagnetic field sensing coils, and a user interface adapted to display data received from the antenna array to visually depict a relative position of the antenna array relative to the localizer base.

19 Claims, 10 Drawing Sheets

(52) U.S. Cl.
CPC .............. *A61M 2205/3553* (2013.01); *A61M 2205/502* (2013.01)

(56) References Cited

U.S. PATENT DOCUMENTS

| | | | |
|---|---|---|---|
| 5,527,307 A | 6/1996 | Srisathapat et al. | |
| 5,702,372 A | 12/1997 | Nelson | |
| 5,833,654 A | 11/1998 | Powers et al. | |
| 5,957,890 A | 9/1999 | Mann et al. | |
| 6,013,051 A | 1/2000 | Nelson | |
| 6,042,579 A | 3/2000 | Elsberry et al. | |
| 6,572,583 B1 | 6/2003 | Olsen et al. | |
| 6,852,106 B2 | 2/2005 | Watson et al. | |
| 6,962,577 B2 | 11/2005 | Tallarida et al. | |
| 7,351,239 B2 | 4/2008 | Gill | |
| 7,366,562 B2 | 4/2008 | Dukesherer et al. | |
| 7,637,897 B2 | 12/2009 | Ginggen | |
| 7,803,143 B2 | 10/2010 | Tallarida et al. | |
| 7,963,956 B2 | 6/2011 | Kunst | |
| 8,320,991 B2 | 11/2012 | Jascob et al. | |
| 8,419,710 B2 | 4/2013 | Keimel et al. | |
| 8,483,802 B2 * | 7/2013 | Kalpin .............. | A61M 39/0208 |
| 8,545,484 B2 | 10/2013 | Haase et al. | |
| 8,591,456 B2 | 11/2013 | Steinbach | |
| 8,613,724 B2 | 12/2013 | Lanier, Jr. et al. | |
| 8,721,605 B2 | 5/2014 | Brandt et al. | |
| 8,915,893 B2 | 12/2014 | Steinbach | |
| 8,932,271 B2 | 1/2015 | Hamatake et al. | |
| 9,079,004 B2 | 7/2015 | Wiley et al. | |
| 9,427,553 B2 | 8/2016 | Nelson | |
| 9,433,764 B2 | 9/2016 | East et al. | |
| 9,744,338 B2 | 8/2017 | East et al. | |
| 9,782,536 B2 | 10/2017 | Skutnik et al. | |
| 9,919,102 B2 | 3/2018 | John | |
| 9,981,117 B2 | 5/2018 | Brandt et al. | |
| 9,993,600 B2 | 6/2018 | Lanier, Jr. et al. | |
| 10,238,851 B2 | 3/2019 | Butziger et al. | |
| 10,376,635 B2 | 8/2019 | Haase | |
| 10,589,024 B2 | 3/2020 | John | |
| 10,596,362 B2 | 3/2020 | Fielder et al. | |
| 10,625,060 B2 | 4/2020 | Børgesen | |
| 2005/0124980 A1 | 6/2005 | Sanders | |
| 2005/0137537 A1 | 6/2005 | Watson et al. | |
| 2007/0112291 A1 | 5/2007 | Børgesen | |
| 2010/0030196 A1 | 2/2010 | Hildebrand et al. | |
| 2011/0193688 A1 * | 8/2011 | Forsell .................. | 340/10.4 |
| 2016/0089521 A1 | 3/2016 | Dragoon et al. | |
| 2017/0325685 A1 | 11/2017 | Shachar et al. | |
| 2018/0117243 A1 | 5/2018 | Maguire | |
| 2018/0303600 A1 * | 10/2018 | McClellan .............. | A61B 90/02 |
| 2019/0009014 A1 | 1/2019 | Chen et al. | |
| 2019/0184139 A1 | 6/2019 | Nelson et al. | |
| 2019/0255284 A1 * | 8/2019 | Freund et al. .... | A61M 39/0208 |
| 2019/0269850 A1 | 9/2019 | Shih et al. | |
| 2020/0061362 A1 | 2/2020 | Singh et al. | |
| 2020/0367856 A1 * | 11/2020 | Huffer et al. ........ | A61B 8/4254 |
| 2021/0260280 A1 * | 8/2021 | Gordon et al. ... | A61M 39/0247 |

FOREIGN PATENT DOCUMENTS

| | | |
|---|---|---|
| WO | WO2012138854 A1 | 10/2012 |
| WO | WO2013134486 A4 | 9/2013 |
| WO | WO2016059162 A1 | 4/2016 |
| WO | WO2020046791 A1 | 3/2020 |

* cited by examiner

DRUG INFUSION PORT

TECHNICAL FIELD

The present technology is generally related to implantable medical devices, and more particularly to implantable medical ports for managing the delivery and dispensation of prescribed therapeutic agents.

BACKGROUND

Implantable medical devices, such as implantable medical ports, are useful in managing the delivery and dispensation of prescribed therapeutic agents, nutrients, drugs, medicaments such as antibiotics, blood clotting agents, analgesics and other fluid or fluid like substances (collectively "medicaments" or "infusates") to patients in volume- and time-controlled doses as well as through boluses. Such implantable ports are particularly useful for treating diseases and disorders that require regular or chronic (i.e., long-term) pharmacological intervention, including tremor, spasticity, multiple sclerosis, Alzheimer's disease, Parkinson's disease, amyotrophic lateral sclerosis (ALS), Huntington's disease, cancer, epilepsy, chronic pain, urinary or fecal incontinence, sexual dysfunction, obesity, and gastroparesis, to name just a few. Depending upon their specific designs and intended uses, implantable ports are well adapted to administer infusates to specific areas within the vasculatures and central nervous system, including the subarachnoid, epidural, intrathecal, and intracranial spaces or provide access to those spaces for aspiration.

Providing access to the cerebrospinal fluid for the administration of medicament or aspiration of fluid has a number of important advantages over other forms of medicament administration. For example, oral administration is often not workable because the systematic dose of the substance needed to achieve the therapeutic dose at the target site may be too large for the patient to tolerate without adverse side effects. Also, some substances simply cannot be absorbed in the gut adequately for a therapeutic dose to reach the target site. Moreover, substances that are not lipid soluble may not cross the blood-brain barrier adequately if needed in the brain. In addition, infusion of substances from outside the body requires a transcutaneous catheter or access with a hypodermic needle, which results in other risks such as infection or catheter dislodgment.

Implantable medical devices often include an implantable catheter in fluid communication with an implantable access port. The implantable access port is often placed over the ribs, cranially or in another location, and is connected to the implantable catheter. The catheter is generally configured as a flexible tube with a lumen running the length of the catheter to a selected delivery site in the body, such as the intracranial or subarachnoid space. When it is desirable to administer a medicament, a needle is inserted through the patient's skin, and through a septum of the implantable port, which is in fluid connection with the catheter. The medicament is then injected into the implantable port where it flows through the implantable port and catheter for administration into the patient.

SUMMARY OF THE DISCLOSURE

When accessing the implantable access port to infuse medicament, it is important that the supply system delivering medicament to the implantable port pierce the septum of the implantable port, as potentially adverse side effects may occur if the medicament is delivered to a location other than the chamber within the implantable port. For example, if the portion of the supply assembly employed to deliver the medicament to the implantable medical device is not properly positioned, the medicament can be injected directly into a pocket surrounding the implantable port. Applicants of the present disclosure have developed systems and methods to address this concern.

The techniques of this disclosure generally relate to implantable systems and methods with port finding capabilities to facilitate healthcare providers in locating the access port of an implantable medical device beneath the skin of a patient. In some embodiments, one or more navigational components can be configured to determine precise orientation and position of a delivery system relative to an implanted or implantable medical device. In some embodiments, the implantable medical device can include a localizer formed of one or more transmitting coils that transmit a navigation region or field, as an aid in properly locating the access port.

Recent developments in medical science have led to the development of new types of therapy in the treatment of debilitating neurodegenerative diseases, such as Huntington's disease, Spinal Muscular Atrophy (SMA), survival motor neuron (SMN) deficiency, amyotrophic lateral sclerosis (ALS), Angelman's Syndrome, Dravet Syndrome, Alzheimer's disease, progressive supranuclear palsy (PSP), frontotemporal dementia (FTD), Parkinson's Disease, central nervous system (CNS) lymphoma, and Leptomeningeal Cancer, among others. Such treatments may require chronic bolus administration of antisense oligonucleotides and/or gene therapy into the intrathecal space of the patient according to a prescribed schedule. Traditional methods of accessing the intrathecal space include lumbar puncture, which often requires anesthesia and radiographic imaging, and includes exposure risks associated with deleterious side effects.

Applicants of the present disclosure propose alternative medicament delivery systems and methods, including targeted drug delivery via an implanted catheter extending into the subarachnoid, epidural, intrathecal, or intracranial space of a patient. According to such delivery systems and methods, the implanted catheter can be in fluid communication with a medical port, thereby enabling the healthcare provider to repeatedly administer medicament, without the risks and complications associated with traditional methods of accessing these spaces. Further, such systems and methods are designed to facilitate intrathecal access in patients with spinal deformities and/or instrumentation for whom intrathecal access, and the associated fluid administration and sampling via lumbar puncture is complicated or not possible. By utilizing the devices, systems, and methods provided, the need for repeat anesthesia and surgery each time intrathecal access is desired can be avoided. Moreover, by simplifying and eliminating many of the risks associated with the treatment, the treatments can be performed outside of the normal clinic settings, for example in the home of a patient.

As previously acknowledged, properly locating an access port for administration of medicament can present its own challenges, which can prolong the medical procedure with the risk of inadvertently injecting the medicament into the tissue surrounding the implantable medical device (commonly referred to as a "pocket fill"). Traditional methods of locating the access port of an implanted medical device include palpation of the patient, and accessing a septum of the access port with a needle of a delivery system, such as a standard non-coring Huber needle. In some cases, palpation can be confirmed by tactile features or vibrating piezoelectric elements positioned on the implantable medical device. Other methods of locating the access port include the use of Hall Effect sensors, LEDs to provide illumination through the tissue, and magnets as an aid in proper positioning of the delivery system. Unfortunately these methods can lack the ability to determine the orientation of the delivery system relative to the implanted medical device and the precise location of the port.

Applicants of the present disclosure have addressed this concern through the development of implantable systems and methods with "port finder" capabilities to facilitate healthcare providers in positively locating the access port of an implantable medical device beneath the skin of the patient. In some embodiments, the implantable systems and methods can include a localizer formed of one or more transmitting coils that transmit a navigation region or field as an aid in determining the orientation of the delivery system relative to the precise location of the port or septum.

One embodiment of the present disclosure provides a medical system configured to aid a user in locating an access port of an implantable medical device. The medical system can include an implantable port, a localizer base, an antenna array, and a user interface. The implantable port can include a medicament chamber accessible through a septum. The localizer base can be operably coupled to the implantable port, and can include an array of electromagnetic field emitting coils. The antenna array can include a plurality of electromagnetic field sensing coils. The user interface can be adapted to display data received from the antenna array to visually depict a relative position of the antenna array relative to the localizer base.

In one embodiment, the localizer base can include three electromagnetic field emitting coils forming a tri-lobed localizer base. In one embodiment, the array of electromagnetic field emitting coils can be in the form of a printed circuit board. In one embodiment, the array of electromagnetic field emitting coils can be configured to operate in a frequency range of between about 10 kHz and about 50 kHz. In one embodiment, the localizer base can further include a processor and power source. In one embodiment, the power source can be an induction coil. In one embodiment, the induction coil can further be configured to serve as a telemetry antenna.

In one embodiment, the medical system can further include a supply assembly including a syringe configured to contain medicament and a septum piercing needle. In one embodiment, the antenna array can include a plurality of coil groups, each coil group including three individual coils positioned along a respective x-, y-, and z-axis. In one embodiment, the coil groups can be positioned in the vertices of a tetrahedron. In one embodiment, each side of the tetrahedron can measure between about 8 mm and about 15 mm in length.

Another embodiment of the present disclosure provides an implantable port configured to aid a user in locating a septum for administration of medicament. The medical system can include an implantable port including a medicament chamber accessible through a septum, and a localizer base operably coupled to the implantable port including an array of electromagnetic field emitting coils.

Yet another embodiment of the present disclosure provides a method of aiding a user in locating an access port of an implantable medical device, comprising: providing an implantable port comprising a medicament chamber accessible via a septum and an array of electromagnetic field emitting coils; providing an antenna array comprising a plurality of electromagnetic field sensing coils; and displaying data from the antenna array to visually depict a position of the antenna array relative to the localizer base.

The details of one or more aspects of the disclosure are set forth in the accompanying drawings and the description below. Other features, objects, and advantages of the techniques described in this disclosure will be apparent from the description in the drawings, and from the claims.

BRIEF DESCRIPTION OF THE DRAWINGS

The disclosure can be more completely understood in consideration of the following detailed description of various embodiments of the disclosure, in connection with the accompanying drawings, in which.

Figure 1:
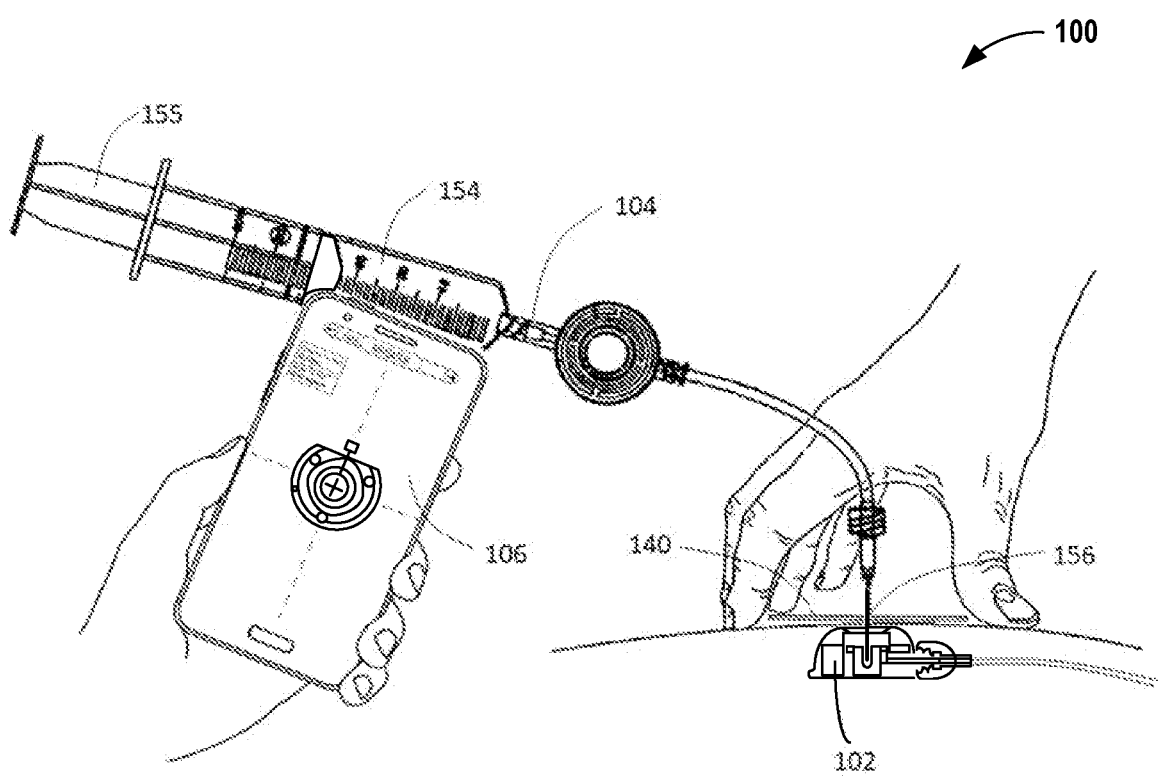
FIG. 1 is a schematic view depicting a medical system, in accordance with an embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Referring to FIG. 1, a medical system 100 with port finding capabilities to facilitate a healthcare provider in locating an access port of an implantable medical device beneath the skin of a patient is depicted in accordance with an embodiment of the disclosure. In some embodiments, the medical system 100 can include an implantable medical device 102 configured to transmit a navigation region or field, a supply assembly 104 configured to receive the transmitted navigation region or field, and an optional user interface 106 configured to use the received navigational region or field information to provide an aid to healthcare providers in properly positioning the supply assembly 104 relative to the implantable medical device 102. The term "healthcare provider: as used herein, refers to a doctor, nurse, clinician, assistant, or user of the medical system 100, implantable medical device 102, or associated methods described herein, and may occasionally be referred to herein as a "user."

Figure 2:
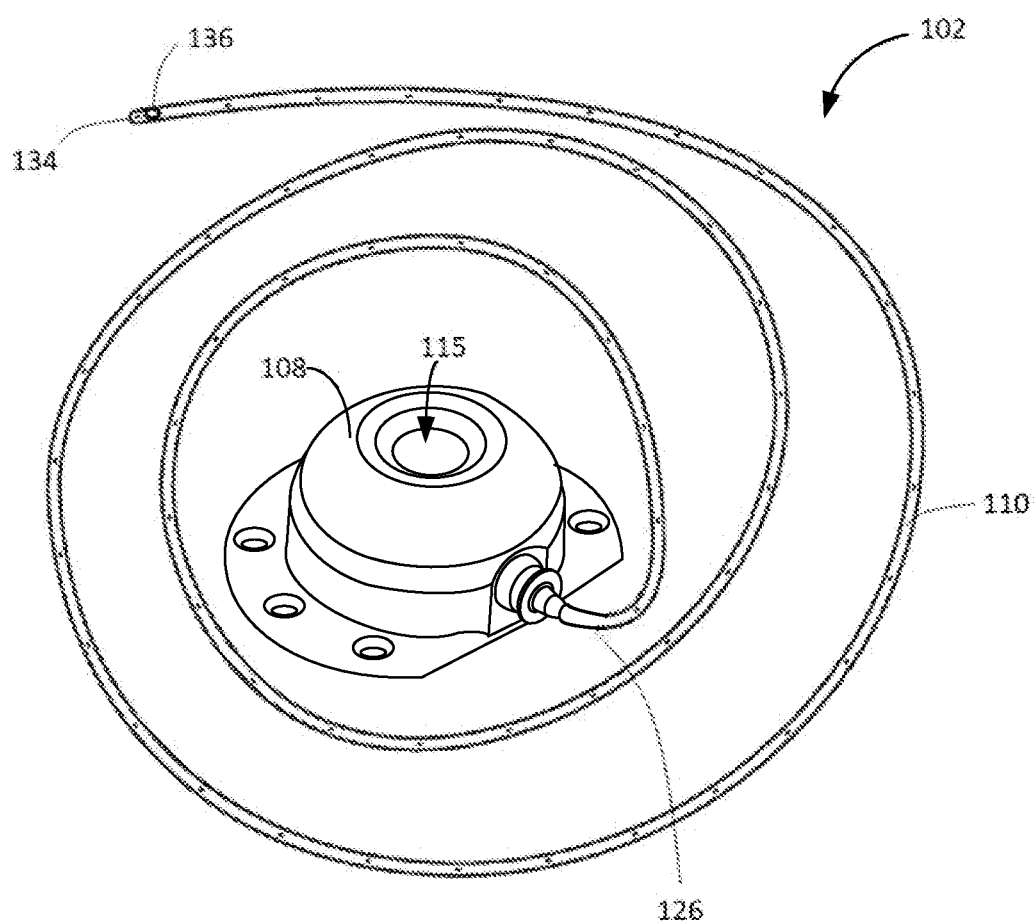
FIG. 2 is a perspective view depicting an implantable medical device, in accordance with an embodiment of the disclosure.
Figure 3:
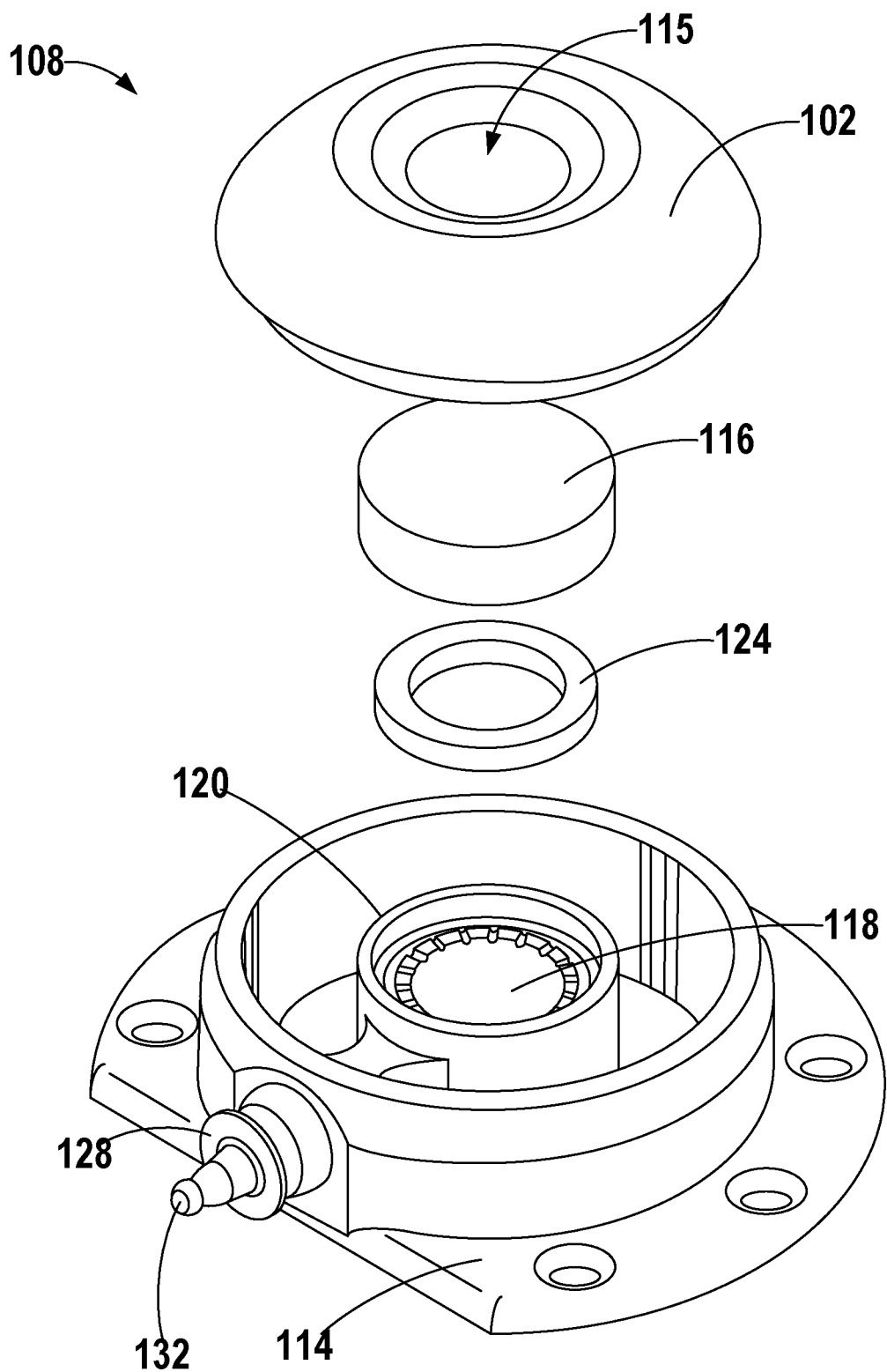
FIG. 3 is an exploded, perspective view depicting an implantable port, in accordance with an embodiment of the disclosure.

FIGS. 2 and 3 show an embodiment of an implantable medical device 102 (which is configured to emit a navigation field) in the form of an implantable port 108 in fluid communication with an implantable catheter 110. In particular, FIG. 2 depicts a perspective view of the implantable port 108 and catheter 110 configured to transmit a navigation field, while FIG. 3 depicts an exploded perspective view of an implantable port 108 configured to transmit a navigation field.

With additional reference to FIGS. 2 and 3, an embodiment of an implantable medical device 102 configured to transmit a navigation field in the form of an implantable port 108 in fluid communication with an implantable catheter 110 is depicted in accordance with an embodiment of the disclosure. In particular, FIG. 2 depicts a perspective view of the implantable port 108 and catheter 110 configured to transmit a navigation field, while FIG. 3 depicts an exploded perspective view of an implantable port 108 configured to transmit a navigation field.

The implantable port 108 can include a generally dome-shaped upper housing 112 and a disk-shaped lower housing 114. Upper and lower housings 112, 114 can be constructed of a body-tolerant material such as titanium or a body-compatible plastic, and sealed to one another about their periphery. The upper housing 112 can define an access port 115 to provide access to a centrally-located septum 116. The septum 116 can define an upper boundary of a chamber 118. A chamber wall 120, which in some embodiments is substantially cylindrical in shape, can define the walls 120 of the chamber 118. The chamber wall 120 can be made of a rigid material, such as a biocompatible polymer or titanium. In one embodiment, the septum 116 can be constructed of a resilient, pliable material such as a self-sealing silicone rubber. In some embodiments, a fill port washer 124 can be positioned between the septum 116 and the chamber wall 120.

In some embodiments, an optional needle screen (not depicted) positioned adjacent to the septum 116 can inhibit needles having a diameter larger than a given diameter from passing therethrough while allowing needles having diameters that are smaller than the given diameter to pass therethrough. In some embodiments, a needle stop can rest on the lower housing 114. In some embodiments, the implantable catheter 110 can be connected to the implantable port 108 by sliding a proximal end 126 of the catheter 110 over a catheter fitting 128 of the implantable port 108. The catheter fitting 128 can be operably coupled to the upper and lower housings 112, 114, for example via an O-ring. The catheter fitting 128 can be in fluid communication with the chamber 118 via conduit 132.

With reference to FIGS. 1-3, a quantity of medicament can pass from a supply assembly 104 external to the patient, through the implantable port 108 to a distal end 134 of the catheter 110. In particular, to administer medicament, a needle of a supply assembly 104 filled with the medicament can be passed through a patient's skin, through the access port 115 and into the septum 116 to enter into the chamber 118. As the medicament is expelled from the supply assembly 104, the medicament fills the chamber 118, passes through the conduit 132 and into a lumen of the catheter 110 generally extending between the proximal end 126 and an infusion port 136 in proximity to the distal end 134. In some embodiments, the infusion port 136 can be positioned on the distal end or tip 134 of the catheter 110. Alternatively, as depicted, the infusion port 136 can be positioned proximally from the distal tip 134 along the body of the catheter 110.

In some embodiments, the chamber 118 of the implantable port 108 can be impregnated or pre-loaded with one or more dosages of medicament. Thereafter, a healthcare provider can dispense one of the doses by applying pressure to the septum 116 or other movable portion of the port 108 to force the dose through the conduit 132 and into the catheter 110. If more than one dose is provided, the dosages can be separated by movable doors (not depicted) extending across the chamber 118. For example, in some embodiments, the doors can be constructed of a ferritic material and be selectively and non-invasively moved by a clinician using an external device having one or more magnets therein.

The distal tip 134 of the catheter 104 can be positioned at a desired site within the patient for administration of medicament, for example within the intrathecal space of the patient, among other desirable targeted drug delivery sites. Accordingly, the catheter 110 can provide a substantially homogeneous delivery of medicament to the intrathecal space or other desirable targeted drug delivery site of a patient. As such, the catheter 110 can be configured to extend along substantially the entire length of a patient's spinal column or along any portion thereof.

In some embodiments, the catheter 110 can be configured for long term implantation into a patient and, as such, can be constructed from materials to make the catheter soft, flexible, and kink resistant. Further, in some embodiments, the catheter 110 can be configured to accommodate complex spine patients (e.g., scoliosis), the materials can provide column strength, break resistance, and stiffness so that the catheter 110 can be threadable during insertion. In some examples, the catheter 110 can be provided with an extended length so that a healthcare provider can cut the catheter 110 to a desired length for a particular patient. In order to confirm that the catheter 110 has been correctly implanted into the intrathecal space and/or is in a fully functioning form, the catheter 110 can include one or more radiopaque markings (not depicted) or components to be visible under imaging.

Figure 4A:
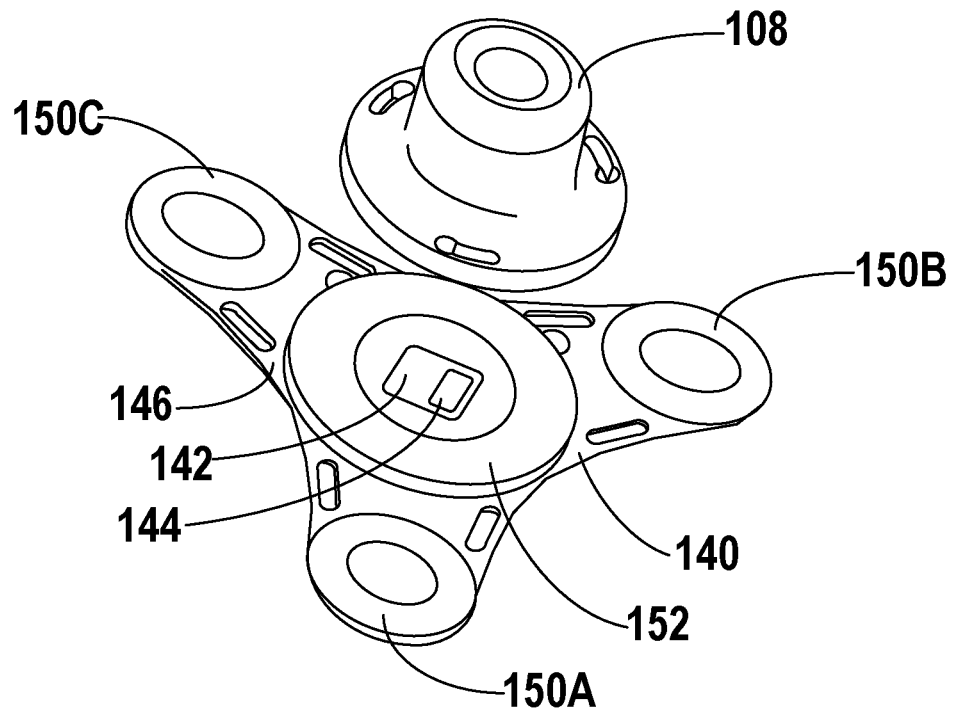
FIG. 4A is an exploded perspective view depicting an implantable port and localizer, in accordance with an embodiment of the disclosure.
Figure 4B:
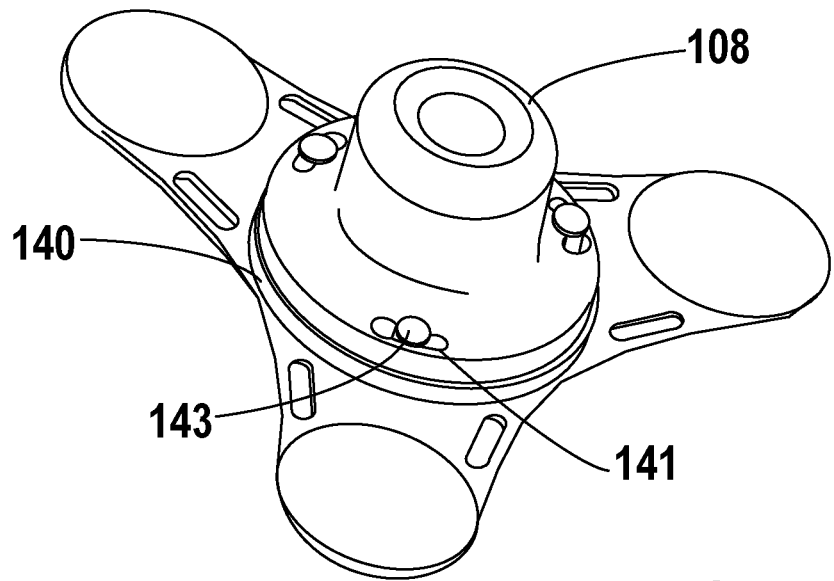
FIG. 4B is a perspective view depicting the localizer base operably coupled to the implantable port of FIG. 4A.
Figure 5:
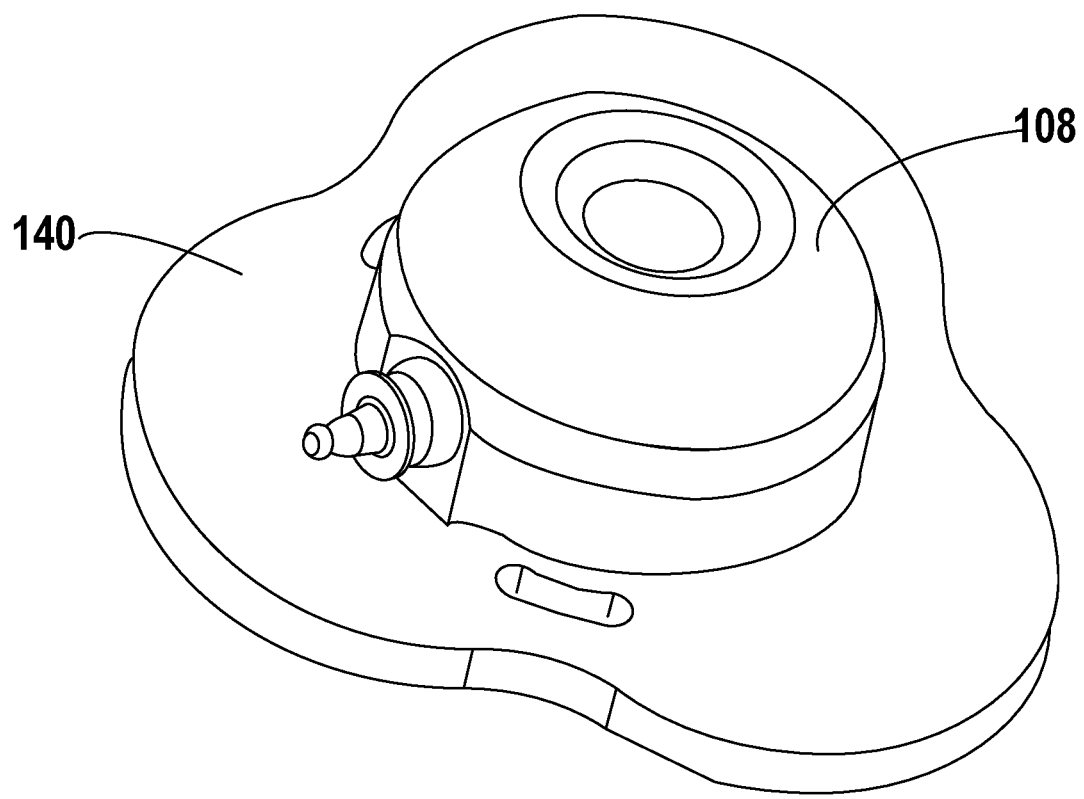
FIG. 5 is a perspective view of an implantable port including a localizer base, in accordance with an embodiment of the disclosure.

With additional reference to FIGS. 4A-B and 5, in some embodiments, the implantable port 108 can be operably coupled to a localizer base 140 configured to transmit an electromagnetic navigation region or field. For example, in some embodiments, the localizer base 140 can house a port finding assembly configured to generate an electromagnetic field, which can optionally be attached to the implantable port 108 at the time of implant. In some embodiments, the localizer base 140 can be configured as a three lobed base structure configured to engage to the suture loops 141 of the implantable port 108, for example via one or more fasteners 143; although other shapes and configurations of base 140, and mechanisms for attaching localizer base 140 to implantable port 108 are also contemplated.

With particular reference to FIG. 4A, in some embodiments, the localizer base 140 can include an electrical circuit 142, for example in the form of a printed circuit board or flex circuit (e.g., an electrical circuit printed or otherwise affixed to a flexible substrate for improved comfort and conformability within the body of the patient). The electrical circuit 142 can include a processor 144, a localizer array 146 and a power source. The processor 144 can be one or more appropriate processors that are selected and used in various implanted medical devices such as the implanted medical device infusion systems sold by Medtronic, Inc. The power source can be in the form of a primary battery, rechargeable battery, or inductive power receiving antenna, and can be configured to provide a supply of electrical power to the processor 144 and localizer array 146 during operation.

In some embodiments, the localizer array 146 can include a plurality of coils 150A-C, each of the coils 150A-C representing one lobe of the tri-lobed localizer base 140. The coils 150A-C can be formed as continuous lengths or spirals of a conductive material, such as copper. In some embodiments, each of the plurality of coils 150A-C can be in the form of a printed circuit board or flex circuit, operably coupled to or integrally formed with the electrical circuit 142. For example, in some embodiments, the coils 150A-C can be formed by appropriate mechanisms including copper deposition methods onto a suitable substrate layer. Although, it should be understood that the coils 150A-C can be formed by other mechanisms including etching, thin wire coiling, deposition, including vacuum, vapor, sputtering, and other appropriate mechanisms or techniques. In some embodiments, coils 150A-C can be formed to include a selected number of turns to achieve appropriate field strength when powered or a current is driven through the coils 150A-C.

The field strength can be selected by the current per conductive path, the number of conductive paths, and the geometry of the conductive paths. For example where the geometries are convex, the area enclosed by the conductive paths can select the field strength. Thus, the field strength can be augmented by selection of turns and the number of coil portions. In addition, the width of the coils or traces of the coil can be selected to achieve the selected number of turns. The number of turns in the coils 150A-C can include about 10 turns to about 100 turns. The number of turns can be selected to achieve a proper density of coil turns in the coil array or field strength. The thickness of the traces or wire can be selected to be about 0.001 inches (in.) (about 0.025 millimeters (mm)) to about 0.01 in. (about 0.25 mm).

Accordingly, the localizer array 146 can be formed of the plurality of coils 150A-C, which as depicted can include three coils; although it is also contemplated that additional numbers of coils could be employed, for example in a stacked or other formation, with optional insulation layers provided between the various coils, such as that described in U.S. Pat. No. 8,483,802 (assigned to Medtronic, Inc.), the contents of which are hereby incorporated by reference herein in their entirety.

As depicted in FIG. 4A, the coils 150A-C of the localizer array 146 can be formed to be substantially annular or ovoid (generally oval) in exterior dimension or shape. For example, as discussed above, traces of the coils 150A-C can be a spiral or coil array of a printed circuit board or flex circuit. Nevertheless, the shape of the coils 150A-C can also be formed in selected shapes. For example, the localizer array 146 can include substantially elliptical coils, ovoid coils or cylindrical coils. By providing the coils in different shapes, substantially all the area of the localizer base 140 can be covered with tracings that define coils of the localizer array 146. However, forming the coils 150A-C as substantially cylindrical or ovoid, can allow for the formation of a substantially uniform field with a minimum resistance in the coil tracings to achieve the appropriate field. As discussed further herein, the coil arrays 150A-C of the localizer array 146 can be used to generate a magnetic field or other navigation region or field that is sensed or received by a corresponding antenna to determine a position of the supply assembly 104 relative to the implanted medical device 102.

FIG. 4A depicts the power source as an induction coil 152, which can be configured to receive power from an external unit, for example in the form of a magnetic or radiofrequency (RF) coupling from a portion of the supply assembly 104. The electrical circuit 142 can convert or otherwise process the received power into a source of usable power by the implantable port 108. The inclusion of an induction coil 152 as the power source, for example in comparison to a primary battery, generally enables the construction of a smaller lighter weight device, thereby facilitating minimally invasive implant patient procedures in which the incision size and time required to implanted anchor the device can be minimized. An induction coil 152 further eliminates the need to remove and replace the power source, as is periodically required of primary batteries.

In some embodiments, the induction coil 152 can further serve as a telemetry antenna, thereby enabling external communication with the processor 144. In some embodiments, the coil 152 (operating as a telemetry antenna) can operate at a selected frequency, such as about 125 (kHz). The frequency of the telemetry system can be used to transmit data to tune the localizer array 146 for optimal performance, or provide other updates to the electrical circuit 142. The coils 150A-C of the localizer array 146 can be operated at other selected frequencies. For example, the coils 150A-C of the localizer array 146 can be operated between about 10 and about 50 kHz. Accordingly, the frequency of the signal transmitted from the telemetry system may generally not interfere with the signal transmitted from the localizer array 146.

Figure 6:
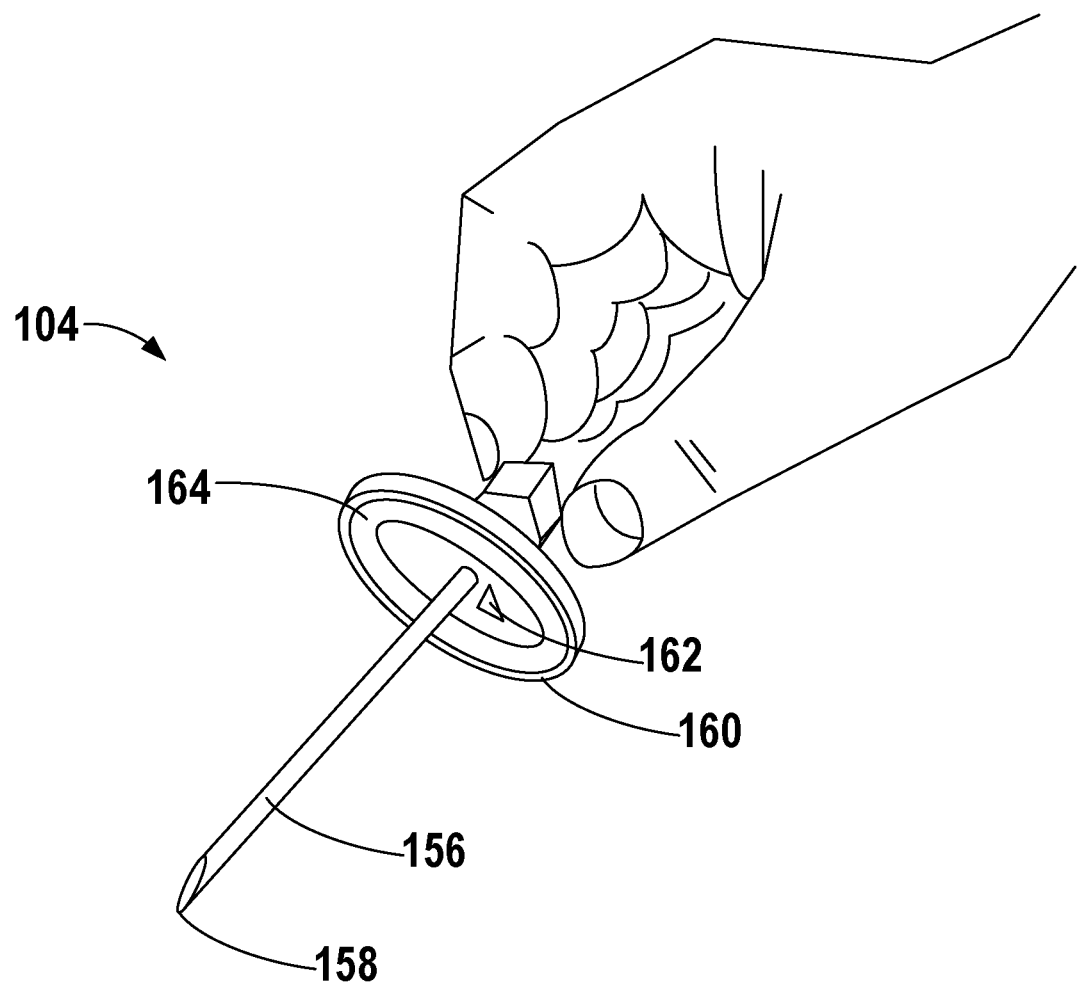
FIG. 6 is a perspective view of a supply assembly, in accordance with an embodiment of the disclosure.

With additional reference to FIG. 6, a supply assembly 104 configured to receive the transmitted navigation region or field from the localizer array 146 of the implantable medical device 102, is depicted in accordance with an embodiment of the disclosure. In some embodiments, the supply assembly 104 can incorporate various features of a commercially available supply assembly system. For example, as depicted in FIG. 1, the supply assembly 104 can include a container 154, in the form of a syringe, which can include a plunger 155 moveably coupled to the container 154 to be manually or automatically actuated by a healthcare provider to force the medicament from the supply assembly 104. The supply assembly 104 can also include a piercing member 156 (e.g., a Huber needle), having a sharpened distal tip 158 for piercing the skin of the patient and the septum 116 of the implantable medical device 102. Thus, when in a target position relative to the implantable port 108, the piercing member 156 can pierce the skin of the patient to be received within the access port 115 of the implantable port 108, thereby enabling the medicament to be delivered from the supply assembly 104 to the implantable port 108.

Figure 7:
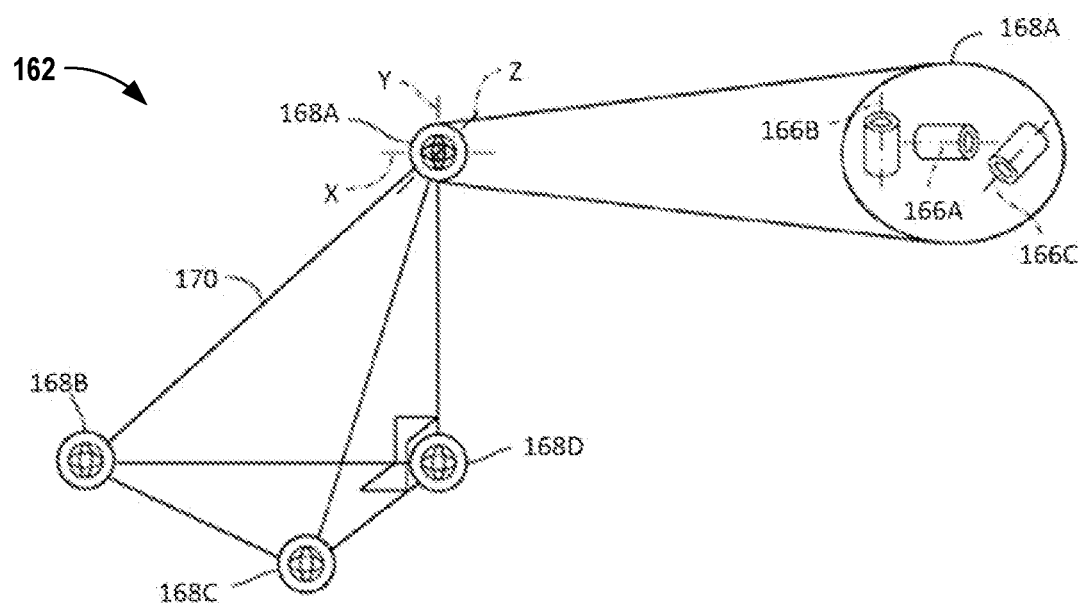
FIG. 7 is a schematic view depicting an antenna array, in accordance with an embodiment of the disclosure.

The supply assembly 104 can further include electronics 160, which can include an antenna array 162, and optional induction coil 164 configured to selectively provide electrical power to the power source of the localizer base 140. As depicted in FIG. 6, in some embodiments, the electronics 160 can be operably coupled to the supply assembly 104, so as to move with the piercing member 156 during the administration of medicament. In other embodiments, such as that depicted in FIG. 1, the electronics 160 can be positioned adjacent to the skin of the patient prior to the administration of medicament, thereby remaining substantially stationary with respect to the localizer array 146. With additional reference to FIG. 7, the antenna array 162 configured to receive the transmitted navigation region can include a plurality of tracking devices, which can be in the form of one or more coils 166. For example, in one embodiment, antenna array 162 can include a plurality of coils 166A-C formed as a coil group 168A. Each coil group 168A-D can have a selected number of coils 166A-C positioned along an x-, y-, and z-axis having a single origin.

In some embodiments, the antenna array 162 can include four substantially identical coil groups including a first coil group 168A, a second coil group 168B, a third coil group 168C and a fourth coil group 168D. Generally, each of the coils 166 of the coil groups 168A-D can be wound or formed orthogonal to one another. Each of the coil groups 168A-D can sense the field produced by the localizer array 146 in the orthogonal axes and generate signals based on the sensed field.

In some embodiments, each of the coil groups 168A-D can be positioned in the vertices of a tetrahedron 170. The tetrahedron 170 can be a regular or an irregular geometrically shaped three-dimensional figure. For example, a tetrahedron defined by the four coil groups can be a regular tetrahedron, where the tetrahedron has substantially equal length legs or sides. In one embodiment, each side or leg of the tetrahedron 170 can be between about eight millimeters (mm) to about fifteen mm. The volume of the tetrahedron, therefore, can be between about 200 millimeters cubed (mm$^3$) and about 300 mm$^3$. The coil groups 168A-D can be positioned in the tetrahedron array such that the antenna array 162 includes twelve discrete coils 166 configured to receive or sense the field generated by the localizer array 146.

Figure 8:
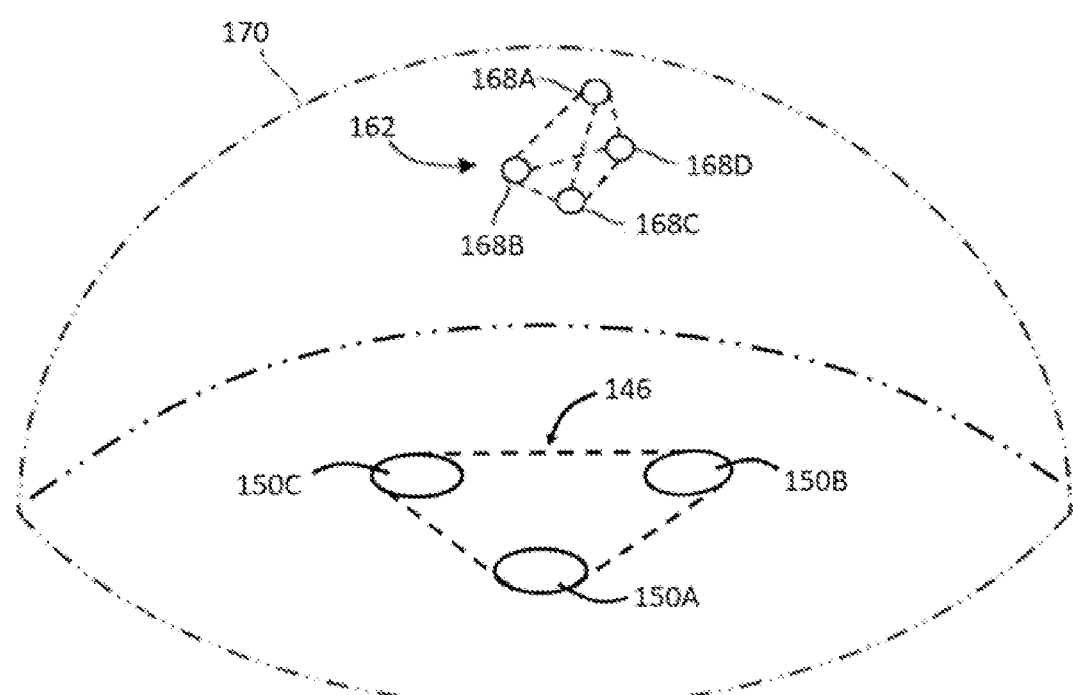
FIG. 8 is a schematic view depicting an interaction between an antenna array and a localizer array, in accordance with an embodiment of the disclosure.

With additional reference to FIG. 8, once the antenna array 162 is positioned within the navigation region 170 emitted by the localizer array 146, the position of the antenna array 162 can be determined, for example via one or more navigational methods disclosed in U.S. Pat. Nos. 7,366,562 and 8,320,991 (assigned to Medtronic, Inc.), the contents of which are hereby incorporated by reference herein in their entirety. By providing the four coil groups 168A-D at positions spaced apart from one another along the legs of the tetrahedron 170, a three-dimensional location including x- y- and z- spatial coordinates and orientation of each of the coil groups 168A-D can be determined. A relative position of the antenna array 162 can then be interpolated (e.g., information sensed by coil groups can be used to determine the position of the antenna array 162 relative to the localizer array 146). The position can then be illustrated on the user interface 106 as discussed further herein to provide information to a healthcare provider for moving the supply assembly 104 relative to the implantable medical device 102.

The antenna array 162 can be used with the localizer array 146 to navigate the supply assembly 104 relative to the implantable medical device 102 for introducing medicament into the chamber 118 of the implantable medical device 102. For example, the supply assembly 104 can be a portable system to be used in a mobile medicine environment, including at home visits by health care providers, as well as in non-surgical outpatient or clinical settings, thereby enabling accuracy in locating the access port 115 and/or septum 116 of an implanted port 108 without requiring large or complex external navigation systems. In some embodiments, the antenna array 162 can be removably attached to the supply assembly 104, such that the antenna array 162 can be used multiple times with multiple patients, which can present a cost savings, as the relatively expensive antenna array 162 can be re-used while the lesser expensive, disposable components of the supply assembly 104 can be discarded.

Accordingly, powering the coils 150A-C of the localizer array 146 can generate an electromagnetic field that can be sensed by the individual coils 166 (comprising coil groups 168) of the antenna array 162, which enables navigation of the supply assembly 104 relative to the implantable medical device 102 to locate the septum 116 of the implantable port 108 with a hypodermic needle 156. By navigating the supply assembly 104 to the implantable medical device 102, a location of the supply assembly 104 can be determined relative to the implantable medical device 102 to identify when the hypodermic needle 156 is at an appropriate location for piercing the septum 116 of the implantable port 108. As discussed further herein, the user interface 106 of the medical system 100 can be used to illustrate the relative positions of the supply assembly 104 and the implantable medical device 102.

Figure 9:
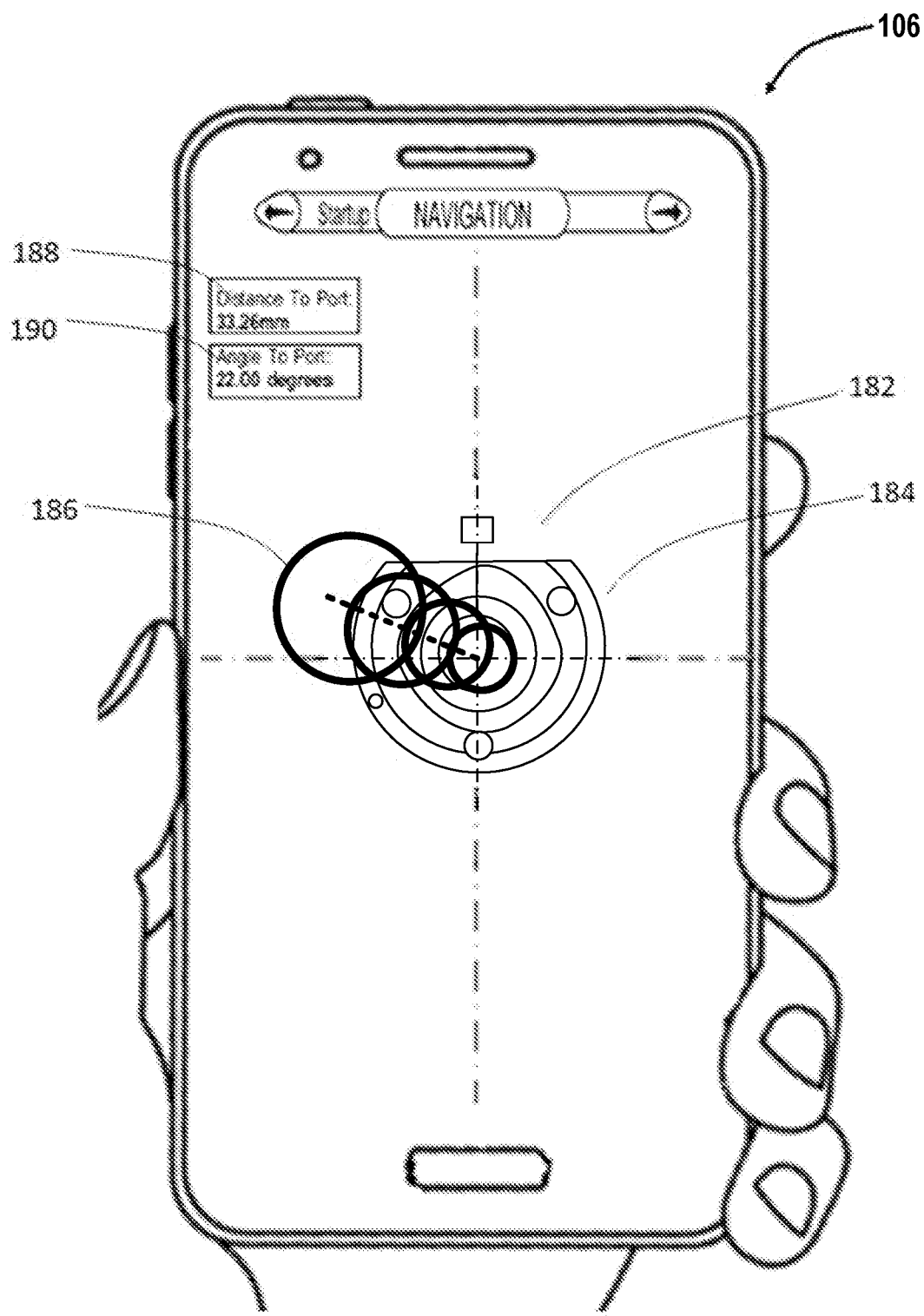
FIG. 9 is a screenshot depicting a user interface configured to visually depict a positional relationship between an antenna array and localizer array, in accordance with an embodiment of the disclosure.

With additional reference to FIG. 9, a user interface 106 configured to use sensed navigational information to provide a visual aid to healthcare providers in positioning a graphic of the supply assembly 182 relative to a graphic of the implantable medical device 184 is depicted in accordance with an embodiment of the disclosure. As further depicted, in some embodiments, the user interface 106 can provide a three-dimensional tracking location of a needle of a supply assembly relative to an access port 115 of an implantable medical device 102 as an aid in ensuring proper positioning of the supply assembly 104 relative to a septum 116 to be pierced by a needle 156 during the administration of medicament.

In some embodiments, the user interface 106 generally comprises a graphical user interface or other appropriate electronic display as an aid in proper positioning of the supply assembly 104 relative to the implantable medical device. For example, the user interface 106 can be viewable on a computer monitor electrically coupled via a wired or wireless connection to the electronics 160 of the supply assembly 104. In embodiments, the user interface 106 can be integrated into a tablet, smart phone, PDA, or other suitable device. Examples of user interactions with the user interface 106 are described herein.

Typically, a healthcare provider can palpate the patient to determine a general or approximate location of the implantable medical device 102 prior to the administration of medicament. After determining the approximate location, the healthcare provider can use the user interface 106 to provide general and detailed guidance information to navigate the needle 156 of the supply assembly 104 to the septum 116 of the implantable port 108. For example, in some embodiments, the healthcare provider can use the user interface 106 as an instrument to effectively "see" the implantable medical device 102 beneath the skin of the patient, as the user interface 106 depicts a graphic 184 representing the overall appearance of the implantable medical device 102.

In some embodiments, a graphic of the supply assembly 182 (e.g., representing needle 156 of the supply assembly 104) can be depicted as crosshairs (representing x- and y-axis components of a relative position of the supply assembly) overlaid on the graphic of the implantable medical device 184. In some embodiments, the graphic of the implantable medical device 184 can remain stationary, while the graphic of the supply assembly 182 moves within the user interface 106 to reflect movement of the actual supply assembly 104 by the healthcare provider. In other embodiments, the graphic of the supply assembly 182 can remain stationary while the graphic of the implantable medical device 184 moves within the user interface 106. In some embodiments, the user interface 106 can further provide one or more graphics 186 representing an angle or z-axis component of the supply assembly. In some embodiments, the user interface 106 can further provide relative distances 188 and angles 190 of the supply assembly 104 relative to the implantable medical device 102; other configurations of user interface 106 are also contemplated.

The system 100 and methods described herein are suitable for administering any fluid composition, such as a pharmaceutical composition comprising one or more therapeutic agents, to a subject. Indeed, the device of the disclosure optionally comprises one or more dosages of a therapeutic agent, such as a therapeutic agent suitable for treating (in whole or in part) a disorder, infection, or injury of the central nervous system or spine. Disorders associated with aspects of the central nervous system or spine include, but are not limited to, spinal muscular atrophy, survival motor neuron deficiency, ankylosing spondylitis, spinal tumors, bipolar disorder, encephalitis, depression, epilepsy, Dravet Syndrome, meningitis, multiple sclerosis, myelopathy, Angelman's Syndrome, CNS lymphoma, Leptomeningeal cancer, Friedreich's Ataxia, hereditary cerebral hemorrhage with amyloidosis-Dutch type (HCHWA-D), cerebral amyloid angiopathy (CAA), amyloid congophilic angiopathy (ACA), and secondary malignant neoplasms (SMN), or neurodegenerative disorders (e.g., Tau protein-related disorders including Alzheimer's disease, Huntington's disease, alpha-synuclei-related disorders including Parkinson's disease, amyotrophic lateral sclerosis (ALS) including superoxide dismutase 1-related ALS, progressive supranuclear palsy, frontotemporal dementia, and Tourette's syndrome. Infections of the CNS include, but are not limited to, viral meningitis, fungal meningitis, epidural infection, viral encephalitis, and neurosyphilis.

Any therapeutic agent may be used in the context of the disclosure. Exemplary therapeutic agents include, e.g., nucleic acids, protein therapeutics, cell therapies, and small molecule therapeutics. Examples of protein therapeutics include antibody-based therapeutics, such as antibodies, antibody fragments, or antibody-like protein products that include binding regions of antibodies (e.g., scFv, diabodies, antibody mimetics, and the like). The antibody-based therapeutic may target, e.g., amyloid plaques, tau proteins, cancer antigens, or abnormal alpha-synuclein. Examples of protein therapeutics also include, but are not limited to, hormones, enzymes (e.g., lysosomal enzymes, such as alpha-L-iduronidase, N-acetylgalactosamine-4-sulfatase, or beta-glucuronidase), growth factors (e.g., fibroblast growth factor (FGF) or neurotrophins or neurotrophic factors, such as glial cell-derived neurotrophic factor (GDNF), brain-derived neurotrophic factor (BDNF), ciliary neurotrophic factor (CNTF), or nerve growth factor (NGF)), blood factors, bone morphogenetic proteins, interferons, interleukins, and thrombolytics. Examples of cell-based therapies include, but are not limited to, stem cell therapeutics and immune cells (including modified immune cells, such as CAR T cells). Suitable small molecule therapeutics include, but are not limited to, analgesics, ion channel blockers, anti-convulsive agents, antibiotics or antiviral agents, anti-inflammatories, anticoagulants, chemotherapeutic, anti-depressants, anti-anxiety agents, steroids, and the like. In various aspects, the therapeutic agent is baclofen, morphine, bupivacaine hydrochloride, clonidine hydrochloride, gabapentin, idursulfase, cytarabine, methotrexate, a corticosteroid, edavarone-conjugate, conotoxin, abomorphine, prednisolone hemisuccinate sodium, carbidopa/levodopa, tetrabenazine, benzodiazepines, such as diazepam and midazolam, alphaxalone or other derivative, cyclophosphamide, idursulfase (Elaprase®), iduronidase (Aldurazyme®), topotecan, buslfan, opmaveloxolone, epicatechin, methylprednisolone, frataxin replacement, reservatrol, nicontinamide, AT-010 (RNA that induces splicing modulation in the mature amyloid precursor protein mRNA), Cerebril™, an anti-Aβ antibody, elenbecestat, a corticosteroid, or nusinersen (Spinraza®), or combinations thereof. In various aspects, the therapeutic agent is a nucleic acid, including DNA or RNA, which may be single stranded or double stranded and which may be modified or unmodified.

Figure 10:
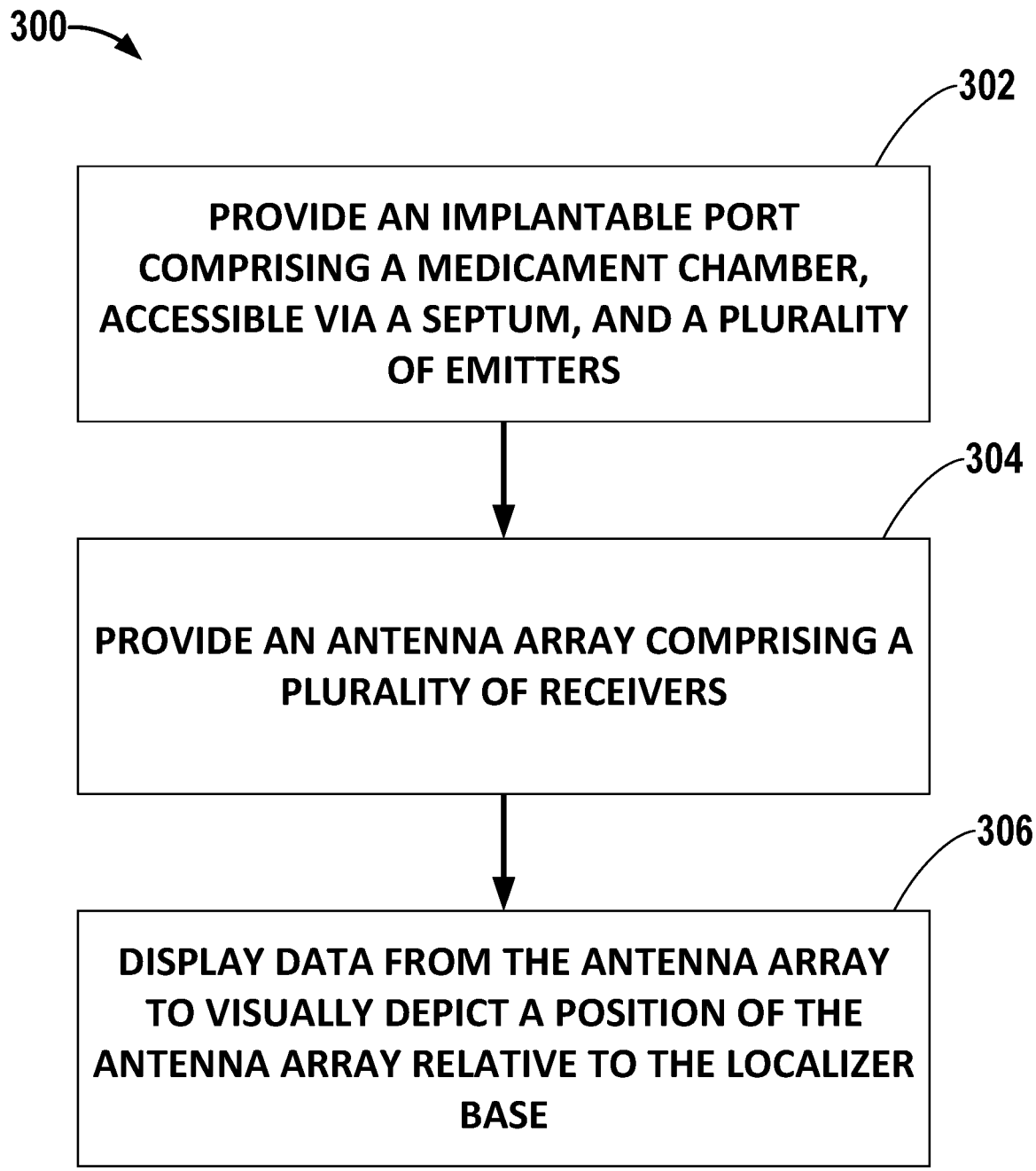
FIG. 10 is a flow chart depicting a method of aiding a user in locating an access port of an implantable medical device, in accordance with an embodiment of the disclosure.

With reference to FIG. 10, a method 300 of aiding a user in locating an access port of an implantable medical device is depicted in accordance with an embodiment of the disclosure. At 302, an implantable port comprising a medicament chamber accessible via a septum and a plurality of emitters can be provided. At 304, an antenna array comprising a plurality of receivers can be provided. At 306, data from the antenna array to visually depict a relative position of the antenna array relative to the localizer base can be depicted. It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

In examples, a system comprising an implantable port comprising a medicament chamber accessible through a septum; a localizer base operably coupled to the implantable port comprising a plurality of emitters; an antenna array comprising a plurality of receivers; and a user interface adapted to display data received by the antenna array to visually depict a relative position of the antenna array relative to the localizer base.

In examples, a system comprising an implantable port including a medicament chamber accessible through a septum; and a localizer base operably coupled to the implantable port including an array of electromagnetic field emitting coils.

In examples, a method comprising providing an implantable port comprising a medicament chamber accessible via a septum and a plurality of emitters; providing an antenna array comprising a plurality of receivers; and displaying data from the antenna array to visually depict a position of the antenna array relative to the localizer base.

In examples, a system comprising an implantable port and a localizer base comprising a plurality of emitters; an antenna array comprising a plurality of receivers; and a computing device configured to: receive data from the antenna array; and display data received by the antenna array to visually depict a relative position of the antenna array relative to the localizer base in real time.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A system comprising:
an implantable port comprising a medicament chamber accessible through a septum;
an implantable localizer base configured to be operably coupled to the implantable port, the localizer base comprising a plurality of emitters exterior to and laterally arranged around the implantable port and configured to emit an electromagnetic field;
an antenna array comprising a plurality of receivers configured to detect the electromagnetic field; and
a computing device configured to:
receive data from the antenna array;
determine, based on the data, a position and an orientation of the antenna array relative to the localizer base; and
output for display via a user interface a visual depiction of the position and the orientation of the antenna array relative to the localizer base.

2. The system of claim 1, wherein the plurality of emitters of the localizer base comprises three electromagnetic field emitting coils collectively forming a tri-lobed localizer base.

3. The system of claim 1, wherein the localizer base comprises a printed circuit board comprising the plurality of emitters.

4. The system of claim 1, wherein the plurality of emitters is configured to operate in a frequency range of about 10 kHz to about 50 kHz.

5. The system of claim 1, wherein the localizer base further comprises a processor and a power source.

6. The system of claim 5, wherein the power source comprises an induction coil.

7. The system of claim 6, wherein the induction coil is further configured to serve as a telemetry antenna.

8. The system of claim 1, further comprising a supply assembly comprising a syringe configured to contain medicament and a septum piercing needle, wherein the antenna array is operably coupled to the supply assembly.

9. The system of claim 1, wherein the plurality of receivers of the antenna array includes a plurality of electromagnetic field sensing coil groups, each coil group including three individual coils positioned along a respective x-, y-, and z-axis.

10. The system of claim 9, wherein the plurality of coil groups is positioned at vertices of a tetrahedron.

11. The system of claim 10, wherein each side of the tetrahedron measures about 8 mm to about 15 mm in length.

12. A system comprising:
an implantable port including a medicament chamber accessible through a septum; and
an implantable localizer base configured to be operably coupled to the implantable port, the localizer base including an array of electromagnetic field emitting coils exterior to and laterally arranged around the implantable port.

13. The system of claim 12, wherein the array of electromagnetic field emitting coils is in the form of a printed circuit board.

14. The system of claim 12, wherein the array of electromagnetic field emitting coils is configured to operate in a frequency range of about 10 kHz to about 50 kHz.

15. The system of claim 12, wherein the localizer base further comprises a processor and a power source.

16. The system of claim 15, wherein the power source comprises an induction coil.

17. The system of claim 16, wherein the induction coil is further configured to serve as a telemetry antenna.

18. The system of claim 1, wherein the implantable port defines one or more suture loops, and wherein the localizer base comprises one or more fasteners configured to removably couple through the one or more suture loops.

19. A method comprising:
receiving, by a computing device, data from an antenna array operably coupled to a syringe and a septum-piercing needle;
determining, by the computing device based on the data, a position and an orientation of the antenna array relative to an implanted localizer base operably coupled to an implanted port, wherein the array comprises a plurality of electromagnetic field emitting coils exterior to and laterally arranged around the implanted port; and
outputting for display, by the computing device, a visual depiction of the position and the orientation of the antenna array relative to the localizer base.

* * * * *